United States Patent [19]

Nowack et al.

[11] Patent Number: 4,605,812
[45] Date of Patent: Aug. 12, 1986

[54] PROCESS FOR REMOVAL OF ARSENIC FROM GASES

[75] Inventors: G. P. Nowack; M. M. Johnson, both of Bartlesville, Okla.

[73] Assignee: Phillips Petroleum Company, Bartlesville, Okla.

[21] Appl. No.: 617,430

[22] Filed: Jun. 5, 1984

[51] Int. Cl.$^4$ .................. C07C 7/148; C10G 29/04
[52] U.S. Cl. ................................ 585/845; 423/210; 208/253; 502/38
[58] Field of Search .......... 423/210 M, 210 R, 210 S; 585/845; 208/253 R; 502/38

[56] References Cited

U.S. PATENT DOCUMENTS

| | | | |
|---|---|---|---|
| 2,511,288 | 6/1950 | Mornll et al. | 252/447 |
| 2,513,508 | 7/1950 | Mornll et al. | 252/431 |
| 2,781,297 | 2/1957 | Appell | 208/253 |
| 2,920,050 | 1/1960 | Blacet et al. | 252/447 |
| 3,112,998 | 12/1963 | Grosskopf | 23/254 |
| 3,542,669 | 11/1970 | DeFeo | 208/91 |
| 3,758,606 | 9/1973 | Horowitz et al. | 585/950 |
| 3,812,652 | 5/1974 | Carr et al. | 55/68 |
| 3,833,498 | 9/1974 | Stahfeld | 208/253 |
| 4,046,679 | 9/1977 | Young | 208/251 H |
| 4,075,085 | 2/1978 | Young | 208/253 |
| 4,088,734 | 5/1978 | Gadelle et al. | 423/210 M |
| 4,354,927 | 10/1982 | Shih et al. | 208/253 |
| 4,462,896 | 7/1984 | Kitagawa et al. | 208/253 |
| 4,532,115 | 7/1985 | Nishino et al. | 423/210 |

FOREIGN PATENT DOCUMENTS

| | | | |
|---|---|---|---|
| 18784 | 1/1982 | Japan | 208/253 |
| 77627 | 5/1982 | Japan | 423/210 |
| 168034 | 4/1985 | Japan | 423/210 |
| 1119720 | 10/1984 | U.S.S.R. | 423/210 |

OTHER PUBLICATIONS

"Reactions of Hydrogen With Organic Compounds Over Copper-Chromium Oxide and Nickel Catalysts", H. Adkins, 1937, pp. 11-25.
"Girdler Catalysts", Girdler Chemical, Inc., Louisville, 1977, pp. 7 and 8.
"Advanced Inorganic Chemistry", F. A. Cotton and G. Wilkinson, Second Edition, 1966, p. 823.
Kirk-Othmer, "Encyclopedia of Chemical Technology", vol. 3, Third Edition, 1978, pp. 257 and 258.
"Comprehensive Inorganic Chemistry", J. C. Bailar et al., 1973, pp. 631-634.

Primary Examiner—Andrew H. Metz
Assistant Examiner—Helane Myers
Attorney, Agent, or Firm—K. K. Brandes

[57] ABSTRACT

Arsines are removed from streams of hydrocarbons or inert gases by contacting the streams with copper (II) chromite catalyst.

21 Claims, No Drawings

PROCESS FOR REMOVAL OF ARSENIC FROM GASES

This invention relates to the treatment of various gases for the removal of arsenic impurities. In an embodiment, the invention relates to methods of removing arsenic impurities from petroleum fractions.

BACKGROUND OF THE INVENTION

The presence of arsenic in its various chemical forms as an impurity in products or feed stocks can be detrimental to the use of such products or feed stocks. For example, the presence of arsenic in even small quantities is undesirable in industrial gases, hydrocarbon feed stocks, fuels, natural gases, liquefied petroleum gases, (LPG) etc. Also, the presence of arsenic in industrial effluent streams such as off-gases from refinery and gasification processes and the like may create health hazards and/or might be subject to environmental controls.

Most crude oils and shale oils contain arsenic in one form or another, typically as arsine and/or alkyl arsines, thus when such oil is cracked, fractionated or otherwise treated to separate petroleum fractions, the resulting petroleum fractions will contain arsenic. When such petroleum fractions are to be subjected to combustion or further treatment, particularly when the treatment involves a catalyst comprising a noble metal, the presence of arsenic is harmful since it can poison the noble metal catalyst. The presence of arsenic is particularly harmful in hydrocarbon fractions which are subjected to further processing in the presence of a catalyst comprising palladium or platinum. Various methods of removing arsenic impurities from gaseous or liquid streams have been developed, but improved processes are still desired.

SUMMARY OF THE INVENTION

An object of this invention is to provide an improved process for the removal of arsenic impurities from gaseous or liquid streams of various chemical compositions. Another object is to provide a process for the removal of arsenic impurities from gaseous hydrocarbon streams, particularly light olefin streams which are to be subjected to catalytic hydrogenation for removal of impurities such as small amounts of diolefins or acetylenes. A further object of this invention is to provide a process for the removal of arsenic impurities from gaseous or liquid streams of hydrocarbons by contacting such streams with a catalytic sorbent. Other objects, advantages and features of the invention will be readily apparent to one skilled in the art from the following detailed description of the invention and the appended claims.

In accordance with the invention, arsines can be removed from gaseous or liquid streams comprising inert or combustible compounds or elements by contacting such streams with a catalytic sorbent comprising copper (II) chromite. Sorbent comprising copper (II) chromite can be contacted with the streams in any suitable form, preferably fixed beds, in which said copper chromite can be composited, preferably with stabilizing and/or promoting materials selected from the group consisting of oxides of alkaline earth metals, i.e. barium, strontium, calcium and magnesium, preferably barium oxide. In a preferred embodiment, a gaseous stream of hydrocarbons is purified by contact with said sorbents. In another preferred embodiment the removal of arsenic impurities from a hydrocarbon stream which is to be further processed by contact with a noble metal catalyst prevents poisoning of said noble metal by arsenic impurities. Streams of unsaturated hydrocarbons such as olefins (including mono-olefins and/or diolefins) can be treated by embodiments of the present invention. Various suitable process conditions can be employed in the practice of the invention, depending upon the nature of the streams to be purified and the characteristics of the catalytic sorbent.

The present invention efficiently removes at least a substantial portion of arsine from such streams in the various forms in which it can be present, e.g. arsine ($AsH_3$) and hydrocarbyl arsines. The arsines involved can be characterized by the formula $AsR_xH_{3-x}$, wherein R is a hydrocarbyl group having from 1 to about 8 carbon atoms and x is 0, 1 or 2. The hydrocarbyl groups can include any radical consisting of carbon and hydrogen, such as, e.g. alkyl, cycloalkyl and aryl groups. Since the exact state in which arsine impurities are present in various streams to be purified is not always known and may even vary during processing, such impurities will be referred to herein simply as "arsines," to include arsine and hydrocarbyl arsines.

DETAILED DESCRIPTION OF THE INVENTION

The present invention can be used to purify any suitable gaseous or liquid stream containing arsines. The invention is particularly effective in the purification of hydrocarbon streams including natural gas and gaseous petroleum fractions comprising hydrocarbons having from 1 to about 9 carbon atoms, such as, e.g. methane, ethane, propane and butane, which are to be subjected to processing with catalysts comprising noble metals. In an embodiment, petroleum fractions comprising hydrocarbons having from 6 to about 9 carbon atoms can be purified prior to their entry into a dehydrogenation or dehydrocyclization process. Non-oxidative gases from coal gasification or natural gases can also be treated by the method of the present invention for removal of arsenic impurities. Various inert and combustible gases can be purified, including inert gases, (e.g. He, Ar, $N_2$), carbon oxides, hydrogen, and the like. However, certain materials which may cause adverse reactions with the catalytic sorbent should be avoided, e.g. sulfur compounds such as $SO_2$ and $H_2S$, and oxides of nitrogen.

Catalytic Sorbent or Reactant-Adsorbent

The catalytic sorbent useful in this invention comprises copper (II) chromite, represented by the formula $Cu(CrO_2)_2$. The copper (II) chromite can be used as such (with or without promoters) or on a carrier. This compound can be prepared by various well-known procedures including the decomposition of copper ammonium chromate, precipitated copper ammonium chromium carbonates or copper-chromium nitrates, or by grinding and heating together copper (II) oxide and chromium (III) oxide. Preparative methods involving the coprecipitation of copper and chromium are presently preferred, as maximum surface area and maximum stability of the +2 valence of copper are obtained thereby.

In a preferred embodiment the copper chromite is promoted by at least one alkaline earth metal oxide, i.e. an oxide of barium, strontium, calcium or magnesium, preferably barium oxide. The alkaline earth metal oxide tends to stabilize the copper in the plus 2 oxidation state and prevent its reduction to a less active form in the plus 1 oxidation state while the catalyst is in use. The presence of the alkaline earth metal oxide also makes the copper (II) chromite more resistant to abrasion and disintegration due to the formation of $Cu_3As_2$ while in use. The alkaline earth metal oxides, when used, can be coprecipitated with the copper and chromium in the preferred preparative method.

Such copper chromite materials are available commercially in either promoted or non-promoted forms from suppliers such as United Catalysts, Inc., Louisville, Ky. 40232.

Depending upon the nature of the process in which the sorbent is to be used, the sorbent can be provided in powder form or in larger particles such as tablets or pellets.

When an alkaline earth metal compound is used to promote or stabilize the copper chromite sorbent, the proportions can be determined by the weight ratio between the alkaline earth metal and chromium in the sorbent. The atomic ratio of alkaline earth metal to chromium (as determined from weight percent and atomic weight of each metal) generally is in the range of from about 1:100 to about 1:2, and is preferably in the range of from 1:50 to 1:3, or more preferably in the range 1:10 to 1:4. As with most catalytic processes, the effectiveness of the catalyst can vary according to the surface area and/or pore volume of the catalyst material. The surface area of the catalytic sorbent is generally in the range of from 10 to about 300$M^2$ per gram, preferably in the range of from about 50 to about 200$M^2$ per gram, and more preferably in the range of from about 50 to about 100$M^2$ per gram. The sorbent pore volume is generally in the range of from about 0.1 to 1.0 cubic centimeters per gram, preferably from about 0.1 to 0.5 cubic centimeters per gram and more preferably from about 0.1 to about 0.3 cubic centimeters per gram.

For the purposes of this application, the composition containing the copper chromite is termed a "sorbent," although that term is not intended to suggest that the arsenic removal is accomplished by simple physical adsorption or chemisorption. While not wishing to be bound by any particular theory, it is believed that some chemical reaction takes place between the arsenic and the sorbent. It is believed that reactions such as the following occur:

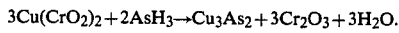

$$3Cu(CrO_2)_2 + 2AsH_3 \rightarrow Cu_3As_2 + 3Cr_2O_3 + 3H_2O.$$

Thus, the chromium is believed to remain in the +3 oxidation state.

As arsine impurities contact, adhere to and react with the sorbent, the capacity of individual molecular units in the catalyst to retain such arsenic impurities is eventually reached and breakthrough occurs.

In this context, the term "breakthrough" means the passage of arsenic beyond or downstream of the sorbent intended to remove it, and is usually expressed as a percentage of the arsenic not removed in relation to the arsenic content of the charged stock. In laboratory evaluations or observations of industrial processes, breakthrough can also be evaluated by the number of hours during which a charged stock containing known concentrations of arsenic impurities can be passed over the sorbent prior to breakthrough occurring.

Once breakthrough occurs and the sorbent material is saturated with arsenic, the process can be continued by replacing the sorbent with fresh material or regenerating the sorbent, e.g., by heating with oxygen so as to convert arsenic to a volatile arsenic oxide and to remove it.

Suitable sorbents comprising copper chromite materials can be designed to purify streams containing arsenic impurities in almost any concentration. However, this process is most effective in removing relatively small concentrations of impurities which are not amenable to removal by other chemical methods. Generally, the concentration of arsenic in the stream to be purified is in the range of from about 10 ppb to about 200 ppm As, preferably in the range of about 50 ppb to 100 ppm As, measured on a weight basis. By using a suitable quantity and type of sorbent comprising copper chromite, the concentration of arsenic impurities can be reduced to concentrations of less than about 10 ppb.

Process Conditions

The catalytic sorbents useful in the invention can be employed in various suitable combinations of process conditions, depending upon the nature of the streams to be purified and the further processing they are to undergo. Temperatures for contacting the stream with the sorbent can be in the range of from about 50° to about 500° F., preferably in the range of from about 100° to about 250° F. For hydrocarbon feed stocks the temperatures are preferably in the range of from about 120° to about 200° F. The invention can be carried out in ambient or elevated pressures in the range of from about 0 to about 3000 psig, preferably in the range of from about 10 to about 2,000 psig. With gaseous streams, the stream to be purified can be passed over the catalytic sorbent at a gas hourly space velocity (GHSV) in the range of from about 100 to about 4,000, preferably in the range of from about 600 to 2,000 volume per volume catalyst per hour.

Treatment of the streams to be purified can be effected in any suitable manner. For example, in a preferred embodiment a bed of the catalytic sorbent is placed as a fixed bed in a confined zone, and a hydrocarbon fraction is passed therethrough in either upward or downward flow. Other suitable, yet less preferred methods of treatment can include a fluidized operation in which a hydrocarbon fraction and the catalytic sorbent particles are maintained in a state of turbulence under hindered settling conditions in a confined zone, moving bed operations in which the catalytic sorbent passes as a moving bed countercurrently to or concurrently with a gaseous petroleum fraction, etc. In a fixed bed operation for a continuous process the flow of fluid can be rotated between two or more copper (II) chromite beds with at least one being in regular operation, the other being in a regeneration mode. The catalyst is believed to be capable of being regenerated. Regeneration can be accomplished by conventional means, preferably by an oxidation step. Continuous processes are preferred, but it is understood that batch type operations can be employed when desired.

A further embodiment of this invention resides in a process for treating hydrocarbons containing both arsine impurities and olefinic impurities. In accordance with this embodiment this hydrocarbon feedstream is first contacted with the copper (II) chromite catalyst as disclosed above to form a substantially arsine free intermediate stream. At least a portion of this stream is then contacted with a noble metal catalyst and hydrogen to remove a significant portion of the olefinic impurities by hydrogenating these compounds to saturated hydrocarbons. The preferred catalyst of this two-step process is one which comprises palladium and/or platinum metal on a solid carrier material.

In yet another embodiment, the process of this invention comprises the use of copper chromite for the removal of arsine impurities from hydrocarbon streams containing at least one of ethane and propane which are to be thermally cracked to produce primarily ethylene and hydrogen, plus "pyrolysis gasoline". The presence of arsine impurities in these products is undesirable, since each of the products, for one reason or another, will subsequently come into contact with a catalyst easily poisoned by arsenic.

In still another embodiment, the inventive process comprises the use of copper chromite to remove arsine impurities from petroleum fractions comprising alkanes having from 6 to about 9 carbon atoms, which are then subjected to dehydrogenation or dehydrocyclization (reforming) processes using noble metal catalyst such as platinum or palladium.

Yet another embodiment of the invention is a process comprising the invention is a process comprising the treatment of mixtures of olefins, e.g. from a catalytic oil cracker off-gas, for removal of $H_2S$ and subsequently for removal of arsines by the method of this invention. Such mixtures of olefins can have from two to about 8 carbon atoms.

Another embodiment is a process for treating a feedstream comprising unsaturated hydrocarbons having from 2 to about 8 carbon atoms and containing arsine impurities, said feedstream being essentially free of acetylenes, comprising the step of contacting the feedstream with copper (II) chromite to substantially reduce the arsine content of the resulting treated feedstream. The treated feedstream can be subjected to the further steps of admixing the stream with a second stream comprising unsaturated hydrocarbons having from 2 to about 8 carbon atoms and containing acetylenic impurities, but essentially free of arsines, and subsequently contacting at least a portion of the resulting admixture with hydrogen and a noble metal hydrogenation catalyst to selectively hydrogenate a substantial portion of the acetylenic impurities to olefins.

The process will be further illustrated by the following non-limiting example.

EXAMPLE I

A stainless steel tube reactor of 0.5 inch diameter and 16 inches length was packed with a 5 inch bottom layer of glass beads, a 5.5 inch middle layer of 20 cc 6/18 mesh barium-promoted copper chromite adsorbent material weighing 27.94 grams, and a 5 inch top layer of glass beads. The promoted copper chromite had a Ba content of about 10 weight percent, a Cr content of about 25 weight percent and Cu content of about 31 weight percent calculated as the metal, a surface area (determined by the BET method with $N_2$) of $75M^2$/gram, and a pore volume (determined by mercury porosimetry at 60,000 psi) of 0.16 cc/gram. The weight ratio of barium to chromium was calculated as about 1:2.5. Thus the atomic ratio of barium to chromium was about 1:6.6. The catalyst was supplied by United Catalyst, Inc., Louisville, Ky. under the product designation Girdler ®G-22.

The reactor was electrically heated to about 150°–155° F. in a hydrogen stream under a pressure of about 200 psig. Then the hydrogen stream was turned off, and a nitrogen feed stream containing 1080 ppm $AsH_3$ was introduced downwardly at a rate of about 13–14 liters/hour (GHSV: 650–700 cc/hr/cc catalyst). The exiting gas stream was first allowed to bubble through two traps in series, each containing 5 cc of a solution of 0.25 weight percent silver diethyl dithiocarbamate in pyridine, for detection of As (detection limit: about 2 ppm), then passed through a trap containing 10 weight percent aqueous HCl, and finally vented.

The arsenic-containing feed stream flowed through the reactor for about 102 hours before a breakthrough of arsenic was detected by a change of color in the first trap. Thereafter, the feed was turned off, and the reactor was allowed to cool in a stream of hydrogen for about 45 minutes. The Ba-promoted copper chromite layer was removed in four portions and analyzed. Results are listed in Table I.

TABLE I

| Cu—Chromite Layer | Weight (Grams) | Weight Percent As | Weight of As (Grams) |
|---|---|---|---|
| First (Top) | 5.62 | 16.6 | 0.93 |
| Second | 6.65 | 19.1 | 1.27 |
| Third | 7.04 | 18.5 | 1.30 |
| Fourth (Bottom) | 11.87 | 17.3 | 2.04 |
| Total | 31.18 | | 5.55 |

Data in Table I show that the Ba-promoted copper chromite absorbent absorbed As up to about 20 percent of its original weight (27.94 g) during the 102 hour run, during which essentially all $AsH_3$ was removed from the feed stream. It is to be noted that the actual weight increase of the catalyst at the end of the test run was only about 12 weight percent because for each gram-atom As absorbed 1.5 gram-atom of O were removed in the form of water as indicated by the chemical reaction equation above.

Similar tests with silica gel and zinc oxide (Girdler G72) gave $AsH_3$ breakthrough, as indicated by a color change of the silver diethyl dithiocarbamate indicator solutions after only about 1 hour at conditions essentially the same as used for the Ba-promoted copper chromite.

While this invention has been described in detail for the purpose of illustration, it is not to be construed as limited thereby, but is intended to cover all the changes and modifications within the spirit and scope thereof.

We claim:

1. A process for removing arsine impurities from a gaseous stream or, alternatively, a liquid stream by contacting said stream with a sorbent consisting essentially of a material selected from the group consisting of (A) copper (II) chromite and (B) copper (II) chromite promoted by at least one alkaline earth metal oxide.

2. A process in accordance with claim 1 wherein said alkaline earth metal oxide is barium oxide.

3. A process in accordance with claim 1 wherein said gaseous stream is selected from the group consisting of hydrocarbons, industrial gases, fuels, inert gases and industrial effluents.

4. A process in accordance with claim 3 wherein said gaseous stream is a stream of hydrocarbons.

5. A process in accordance with claim 3 wherein said gaseous stream is a stream of an inert gas selected from the group consisting of helium, argon and nitrogen.

6. A process in accordance with claim 1 wherein said arsine has the formula $AsR_xH_{3-x}$, wherein each R is a hydrocarbyl group having from 1 to 8 carbon atoms and x is either 0, 1 or 2.

7. A process in accordance with claim 6 wherein at least a portion of said arsine is $AsH_3$.

8. A process in accordance with claim 1 wherein the atomic ratio of said alkaline earth metal to the chromium of said copper chromite in said sorbent material (B) is in the range of from about 1:100 to about 1:2.

9. A process in accordance with claim 8 wherein said ratio is in the range of 1:10 to 1:4.

10. A process in accordance with claim 1 wherein said catalytic sorbent has a surface area in the range of from about 10 to about 300$M^2$ per gram and a pore volume in the range of from about 0.1 to 1.0 cc per gram.

11. A process in accordance with claim 1 wherein the process conditions are maintained in the following ranges:
(a) temperature, from about 50° to about 500° F.,
(b) pressure, from 0 to about 3,000 psig, and
(c) gas hourly space velocity, about 100 to about 4,000 volume per volume catalyst per hour.

12. A process in accordance with claim 1 wherein said gaseous stream is a hydrocarbon stream selected from the group consisting of hydrocarbons having from 1 to 9 carbon atoms, and mixtures thereof.

13. A process in accordance with claim 11 wherein the temperature is in the range of from about 100° to about 250° F., the pressure is in the range of from about 10 to about 2000 psig and the gas hourly space velocity is in the range of from about 600 to about 2000 volume per volume catalyst per hour.

14. A process for the removal of arsine impurities from a gaseous stream selected from the group consisting of hydrocarbons and inert gases comprising the step of contacting said stream with a catalytic sorbent consisting essentially of copper (II) chromite and barium oxide.

15. A process for treating a hydrocarbon feedstream comprising arsine impurities and olefins, which process comprises the steps of:
(a) contacting said feestream first with a sorbent consisting essentially of a material selected from the group consisting of (A) copper (II) chromite and (B) copper (II) chromite promoted by at least one alkaline earth metal oxide, to substantially reduce the arsine content of said feedstream and to produce an intermediate stream,
(b) contacting at least a portion of said intermediate stream with hydrogen and a noble metal hydrogenation catalyst to substantially hydrogenate said olefins present in said intermediate stream, and
(c) recovering a hydrogenated hydrocarbon stream.

16. A process in accordance with claim 15 wherein said noble metal catalyst comprises at least one metal selected from the group consisting of palladium and platinum on a solid support.

17. A process for treating a hydrocarbon feedstream comprising alkanes having from 6 to 9 carbon atoms and containing arsine impurities, said process comprising the steps of:
(a) contacting said feestream with a sorbent consisting essentially of a material selected from the group consisting of (A) copper (II) chromite and (B) copper (II) chromite promoted by at least one alkaline earth metal oxide to substantially reduce the arsine content of said feedstream to produce an intermediate stream,
(b) subjecting said intermediate stream to a dehydrogenation or dehydrocyclization process in which said intermediate stream is contacted with a noble metal catalyst, and
(c) recovering a hydrocarbon product stream produced in step (b).

18. A process for treating a feedstream comprising unsaturated hydrocarbons having from 2 to 8 carbon atoms and containing arsine impurities and $H_2S$, said process comprising the steps of:
(a) treating said feedstream first to substantially reduce the $H_2S$ content of said feedstream and to produce an intermediate stream,
(b) contacting said intermediate stream with a sorbent consisting essentially of a material selected from the group consisting of (A) copper (II) chromite and (B) copper (II) chromite promoted by at least one alkaline earth metal oxide to substantially reduce the arsine content of said intermediate stream, and
(c) recovering a purified stream of unsaturated hydrocarbons.

19. A process for treating a feedstream comprising unsaturated hydrocarbons having from 2 to 8 carbon atoms and containing arsine impurities, said feedstream being essentially free of acetylenes, which process comprises the step of:
(a) contacting said feedstream with a sorbent consisting essentially of a material selected from the group consisting of (A) copper (II) chromite and (B) copper (II) chromite promoted by at least one alkaline earth metal oxide to substantially reduce the arsine content of said feedstream, thus producing a treated feedstream.

20. A process in accordance with claim 19, comprising the further steps of
(b) admixing said treated feedstream with a second stream comprising unsaturated hydrocarbons having from 2 to about 8 atoms and containing acetylenic impurities, said second stream being essentially free of arsines, and then
(c) contacting at least a portion of said admixture of said treated feedstream and said second stream with hydrogen and a noble metal hydrogenation catalyst to selectively hydrogenate a substantial portion of said acetylenic impurities to olefins.

21. A process in accordance with claim 1 comprising the additional step of regenerating said sorbent, after it has been saturated with arsenic, by heating said arsenic-saturated sorbent with oxygen so as to convert arsenic to a volatile arsenic oxide and to remove arsenic oxide.

* * * * *